(12) United States Patent
Brown

(10) Patent No.: US 9,823,187 B2
(45) Date of Patent: *Nov. 21, 2017

(54) CONTACT-FREE PHOTOMIXING PROBE FOR DEVICE AND INTEGRATED CIRCUIT MEASUREMENT OR CHARACTERIZATION

(71) Applicant: Elliott R. Brown, Beavercreek, OH (US)

(72) Inventor: Elliott R. Brown, Beavercreek, OH (US)

(73) Assignee: Wright State University, Dayton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,344

(22) Filed: Nov. 7, 2016

(65) Prior Publication Data

US 2017/0115212 A1    Apr. 27, 2017

Related U.S. Application Data

(63) Continuation of application No. 14/367,570, filed as application No. PCT/US2013/023633 on Jan. 29, 2013, now Pat. No. 9,518,938.

(60) Provisional application No. 61/592,295, filed on Jan. 30, 2012.

(51) Int. Cl.
| | | |
|---|---|---|
| *G01N 21/3563* | (2014.01) | |
| *G01R 31/311* | (2006.01) | |
| *G01N 21/3581* | (2014.01) | |

(52) U.S. Cl.
CPC ..... *G01N 21/3563* (2013.01); *G01N 21/3581* (2013.01); *G01R 31/311* (2013.01)

(58) Field of Classification Search
CPC .......... G01N 21/3563; G01N 21/3581; G01R 31/311
See application file for complete search history.

(56) References Cited

U.S. PATENT DOCUMENTS

| | | | | |
|---|---|---|---|---|
| 5,663,639 A | * | 9/1997 | Brown | ............... H01L 31/0232 |
| | | | | 250/214 A |
| 9,518,938 B2 | * | 12/2016 | Brown | ............... G01N 21/3581 |
| 2012/0051386 A1 | * | 3/2012 | Kim | ..................... H01S 5/1096 |
| | | | | 372/96 |
| 2013/0292586 A1 | * | 11/2013 | Teng | ....................... H01Q 9/16 |
| | | | | 250/504 R |

* cited by examiner

*Primary Examiner* — Jermele M Hollington
*Assistant Examiner* — Zannatul Ferdous
(74) *Attorney, Agent, or Firm* — Walter | Haverfield, LLP; James J. Pingor

(57) ABSTRACT

A device for measuring and characterizing solid-state devices or integrated circuits at RF frequencies up to 1.0 THz and beyond is provided that includes a transmitting photomixing probe structure and a receiving photomixing probe structure. The transmitting photomixing probe structure and the receiving photomixing probe structure are ac-coupled to the solid-state device or integrated circuit in a contact-free manner.

20 Claims, 14 Drawing Sheets

Laser Micromachining of Probes

- Picosecond laser micromachining allows contoured and shaped holes and cuts to be drilled with minimal recast.

Thru Cut on 75-μm LiTaO$_3$ 12-15 μm kerf

Hole Array in 380-μm Si

100-μm diam holes

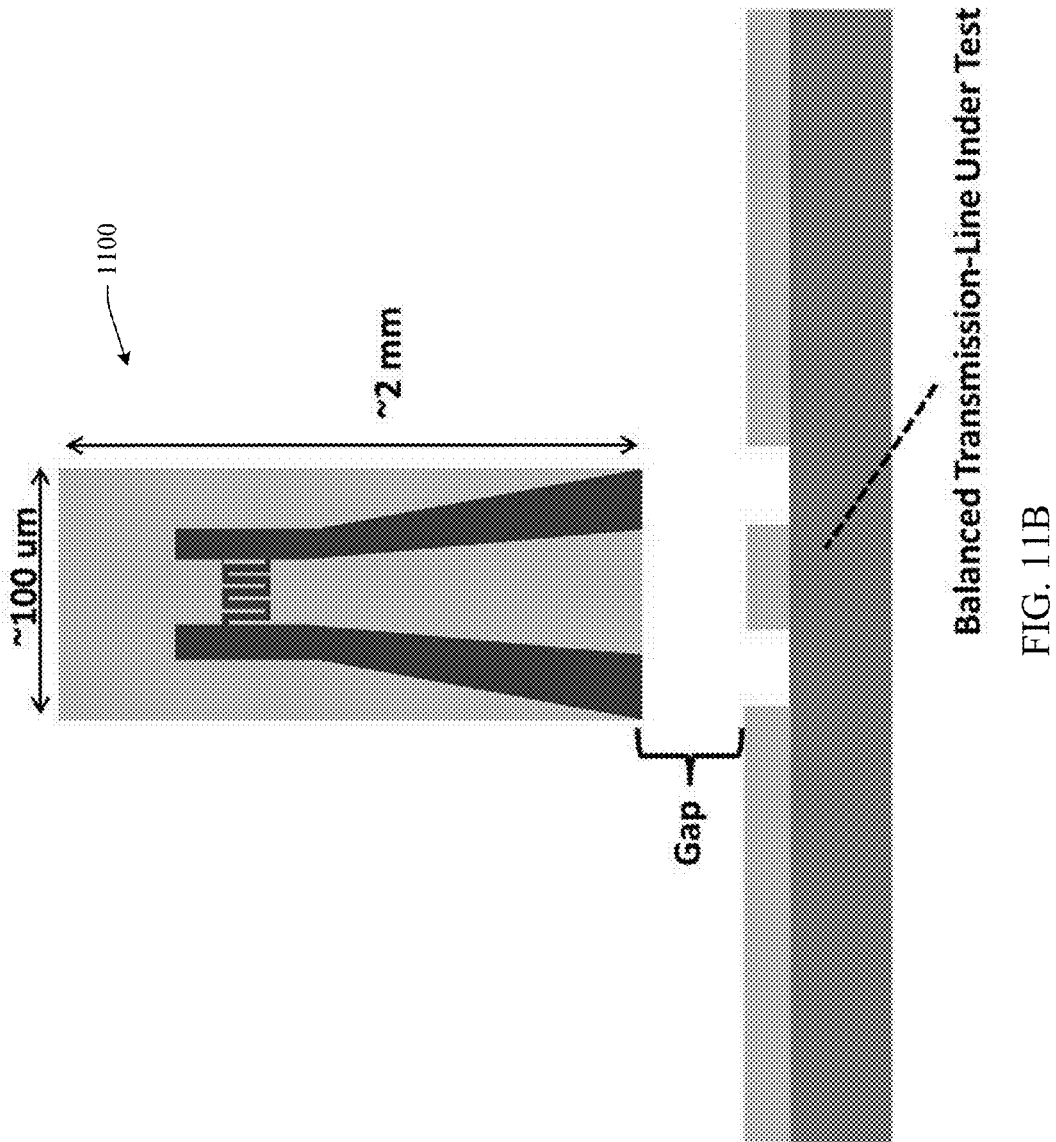

CONTACT-FREE PHOTOMIXING PROBE FOR DEVICE AND INTEGRATED CIRCUIT MEASUREMENT OR CHARACTERIZATION

CROSS-REFERENCE TO RELATED APPLICATIONS

This application is a continuation of U.S. Non-provisional patent application Ser. No. 14/367,570 entitled "CONTACT-FREE PHOTOMIXING PROBE FOR DEVICE AND INTEGRATED CIRCUIT MEASUREMENT OR CHARACTERIZATION" filed on Jun. 20, 2014 which claims priority to and the benefit of International Application No. PCT/US2013/023633, filed Jan. 29, 2013 which claims the benefit of U.S. Provisional Patent A-application Ser. No. 61/592,295, entitled "THz PHOTOMIXING PROBE FOR CONTACT-FREE DEVICE AND INTEGRATED CIRCUIT MEASUREMENT OR CHARACTERIZATION," filed Jan. 30, 2012. The entirety of the above-noted applications are incorporated by reference herein.

NOTICE ON GOVERNMENT FUNDING

This innovation was made with government support under a grant awarded by the Office of Naval Research (ONR) Award N00014-11-1-0721. The government has certain rights in the innovation.

ORIGIN

The innovation disclosed herein relates to contact-free measurement or characterization of solid-state devices or integrated circuits at RF and THz frequencies, and more specifically, to a contact-free, ac-coupled photomixing probe for use in such measurement or characterization.

BACKGROUND

One challenge to the development of THz semiconductor devices, particularly transistors, is THz measurement and characterization. As it stands today, vector network analysis (VNA) with standard (metal-to-metal) dc-coupled contact probing is commercially available up to 500 GHz (Oleson Microwave, http://www.omlinc.com/products/vna-extension-modules/wr-022-325-500-ghz.html) using coaxial probes (GGB Industries, Inc.; PicoProbe Model 325; http://www.ggb.com/325.html), with promise of extending to 750 GHz using silicon-micromachined probes (Dominion MicroProbes, Inc; Model DMPI 1.5V01MPR; http://dm-probes.com/Products%20DMPI.html). However, this technology is very expensive and fragile, with little hope of working beyond 1.0 THz in the foreseeable future, in large part because it requires application of vector network analyzers and custom front-end frequency-extension modules and down-conversion units. The fragility stems from the small size of the ground-signal-ground (GSG) probes and their need to make intimate metal contact. In technical terms, the existing technology couples the conduction current term, J, in Maxwell's equations (specifically, Maxwell's generalization of Amperes Law ($\nabla \times H = J + \partial D/\partial t$)). In circuit terminology, this is "dc coupling."

Photomixing entails the use of two fiber-coupled, frequency-offset diode lasers (usually distributed feedback lasers) to generate or receive a single difference-frequency tone in a photomixer—an ultrafast photoconductive gap easily embedded in a terahertz (THz) antenna or planar transmission line. The tone is "pure" in the sense that there are no harmonics and no intermodulation products of any sort. An important development over the past 10 years is fully-coherent photomixing. There is a transmit (Tx) photomixer and a receive (Rx) photomixer, both driven by the same pair of diode lasers so that the difference frequency tone at each photomixer is mutually coherent. Difference-frequency sweeping occurs by temperature tuning of one or both lasers. Mixing of the Tx-radiated tone with the Rx-generated tone produces a dc component that is easily read out to a transimpedance amplifier. This is the same "homodyne" conversion common in RF and photonic transceivers. To avoid dc-drift and 1/f-noise issues, the Tx photomixer is easily amplitude modulation (AM) or frequency modulation (FM) modulated, and the phase-preserving Rx baseband is raised to the modulation frequency (quasi-homodyne).

SUMMARY

The following is a simplified summary to provide a basic understanding of some aspects of the innovation. This summary is not an extensive overview of the innovation. It is not intended to identify key/critical elements or to delineate the scope of the innovation. Its sole purpose is to present some concepts of the innovation in a simplified form as a prelude to the more detailed description that is presented later.

In accordance with aspects of the innovation, a method for measuring solid-state devices at frequencies up to 1.0 THz and beyond is provided that includes a transmitting photomixing probe structure and a receiving photomixing probe structure. The transmitting photomixing probe structure and the receiving photomixing probe structure are ac-coupled to the solid-state-device circuit in a contact-free manner.

In accordance with another aspect of the innovation, the method utilizes contact-free, ac-coupled probes that are fabricated from the same high-resistivity (e.g., silicon (Si), gallium arsenide (GaAs), indium phosphide (InP), gallium nitride (GaN) etc.) substrates as the photomixers and have either a fork-like or orthorhombic shape for probing balanced THz transmission lines (e.g., coplanar waveguide (CPW)). The ac coupling occurs through polarization current, which is naturally strong in Si, GaAs, InP, and GaN because of their high dielectric constant ($\in \geq 12$) and low THz dielectric loss. And unlike metal-to-metal coupling that becomes increasingly lossy with frequency, dielectric coupling improves approximately linearly with frequency in accordance with Maxwell's equation (Ampere's generalized equation).

The dielectric-coupling probe concept was inspired in part by "electro-optic sampling" first demonstrated in the 1980s and applied to a variety of high-frequency devices and structures in the 1990s Electro-optic sampling is a time-domain technique that takes advantage of the short pulses (~100 fs) and very stable repetition frequency (typically 10 to 100 MHz) of modern solid-state mode-locked lasers (e.g., titanium sapphire). The optical pulses create short THz pulses (typically <1 ps), which then interact with the device or circuit under test, and produce an output that is essentially the impulse response. So like all time-domain techniques, the THz power is spread over 1 THz or more, which degrades the instantaneous signal-to-noise ratio considerably compared to a coherent transceiver. This can be overcome by averaging but then the data acquisition time becomes quite long, on the order of many minutes, which is usually unacceptable for device characterization.

To create the foregoing and related capabilities, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIGS. 11A-B show a plan view of a proposed "orthorhombic" THz probe structure in accordance with aspects of the innovation, and designed with coplanar-waveguide coupling for measuring the signals in similar balanced circuits such as that shown in FIG. 11B.

DETAILED DESCRIPTION

Figure 1:
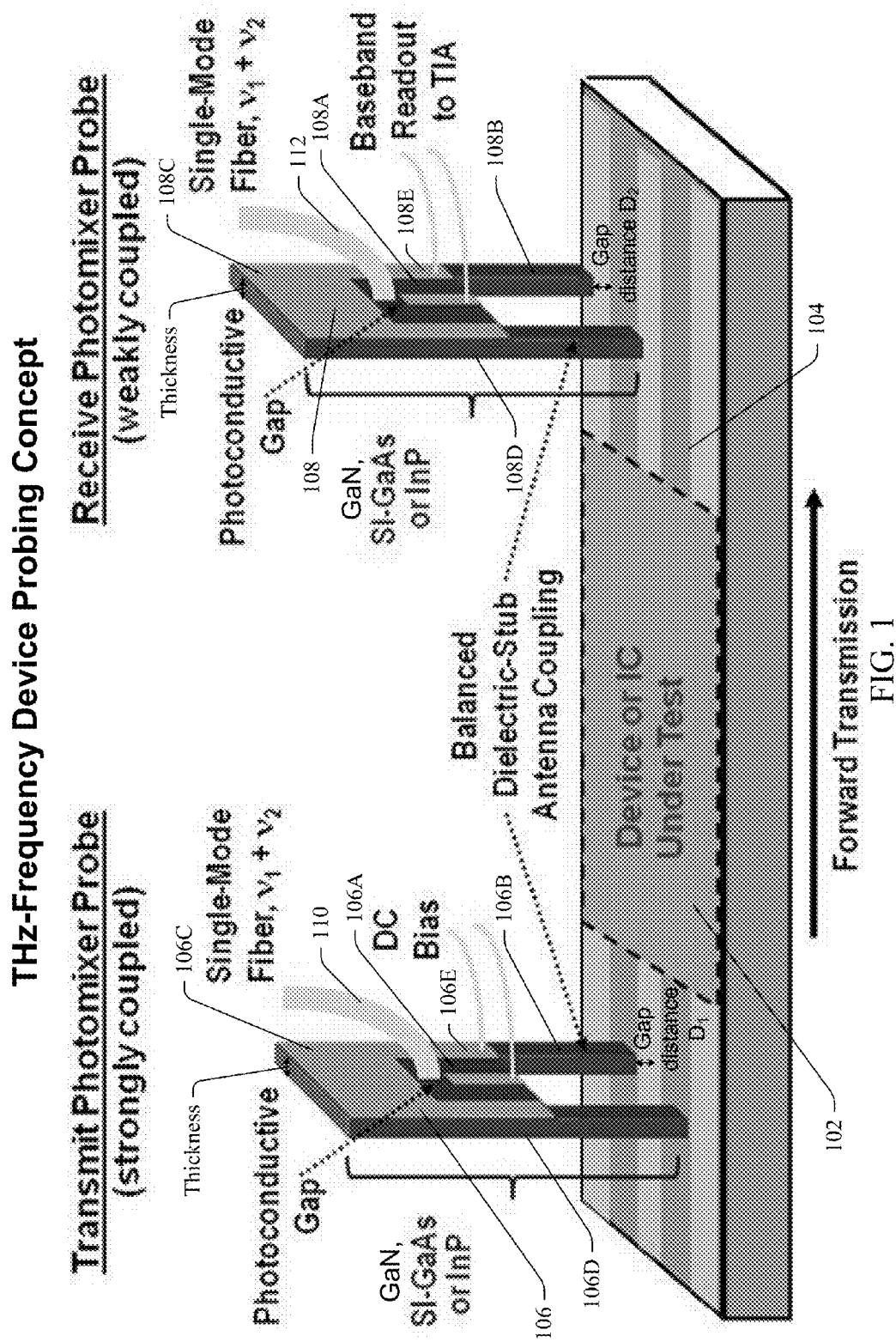
FIG. 1 is a perspective view of THz ac-coupled probe structures coupled to a device in accordance with aspects of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

While specific characteristics are described herein (e.g., specific dimensions of example components, etc.), it is to be understood that the features, functions and benefits of the innovation can employ characteristics that vary from those described herein. These alternatives are to be included within the scope of the innovation and claims appended hereto.

While, for purposes of simplicity of explanation, the one or more methodologies shown herein, e.g., in the form of a flow chart, are shown and described as a series of functions, it is to be understood and appreciated that the subject innovation is not limited by the order of functions, as some may, in accordance with the innovation, occur in a different order and/or concurrently with other functions from that shown and described herein. For example, those skilled in the art will understand and appreciate that a methodology could alternatively be represented as a series of interrelated states or events, such as in a state-flow diagram. Moreover, not all illustrated functions may be required to implement a methodology in accordance with the innovation.

With reference now to the figures, the innovation disclosed herein provides a contact-free system and method of creating an input signal, and probing the output signal of a solid-state device well beyond the frequency limits of existing contact probing. The subject innovation enables operation at higher frequencies and with greater instantaneous bandwidth than currently possible. The approach is to probe the device output by way of the displacement current term ($\partial D/\partial t$), referred to as "ac coupling" in circuit terminology. Although ac coupling is lower in efficiency than dc coupling at microwave frequencies, it becomes increasingly more efficient as the frequency increases. It also improves with the dielectric constant of the coupling material. Accordingly, the innovation disclosed herein can provide a new device measurement and characterization capability at frequencies up to 1.0 THz and beyond the capabilities of existing probing and vector network analysis (VNA) techniques. In addition, the subject innovation allows one to measure and characterize the device without the probes coming into electrical contact with the planar transmission line in which the sample is embedded. As such, the subject innovation avoids the mechanical stress on the probe and scratch-induced damage (of the sample transmission line) that existing contact probe technology entails.

Referring to FIG. 1, illustrated is a perspective view of a solid-state device 102, such as but not limited to a high-speed THz Si-, GaAs-, InP-, or GaN-based semiconductor device, to be tested while embedded in a planar transmission line 104 with the innovative contact-free, ac-coupled probes. In some examples discussed herein, specific examples of a planar transmission line 104 are provided (e.g., a coplanar waveguide (CPW), etc.), but it is to be appreciated that other coplanar transmission lines may be used, such as slot line, microstrip, and twin line. The ac-coupled probes include a transmitting photomixing probe structure, Tx 106, and a receiving photomixing probe structure, Rx 108. Each of the probes 106 and 108 include a photomixer 106A, 108A at the photoconductive gap of the probes. Optical fibers 110, 112 couple the photomixers 106A, 108A, respectively, to two external lasers (not shown). The two lasers need to be mutually coherent, but their frequency difference needs to be tunable. In an aspect of the innovation, both the lasers are single frequency diode lasers. In addition, each of the probes 106 and 108 includes a planar transmission line structure 106C, 108C at the photomixer 106A, 108C end of the probes, where the planar transmission line structure 106C, 108C includes a metalized surface 106E, 108E. Each of the probes 106, 108 is made of a substrate 106D, 108D, and a metalized surface 106E, 108E. In aspects, the substrate 106D, 108D can be made of high resistivity, semiconducting material, including but not limited to, silicon (Si), gallium arsenide (GaAs), indium phosphide (InP), or gallium nitride (GaN). The probes 106 and 108 can have many different designs and some but not all of them will be discussed in connection with FIGS. 3, 4, 11A-B, and 12A-B. In some embodiments of the innovation, such as the examples shown in FIGS. 3 and 4, each of the probes 106 and 108 can also include a dielectric waveguide structure 106B, 108B (without any metalized surfaces) at the circuit end of the probes, where the circuit end of the probes is the end closer to the device or circuit under test. The thickness of the probes 106, 108 can be in the range of 10 to 1000 micron, for example, around 100 micron. The height is in the range of 0.1 to 10 mm, for example, around 1.0 mm. In various aspects, probes 106, 108 can be made using standard semiconductor fabrication and packaging methods, especially if they are made with a silicon substrate.

Coupling to the solid-state device 102 occurs through the dielectric transmitting and receiving photomixing probes 106, 108 acting in part like near-field, dielectric-rod or dielectric-waveguide antennas. The output field of the solid-state device 102 can be sampled in the coplanar-waveguide or other planar transmission line 104 in which the solid-state device 102 is embedded. The gap distances $D_1$ and $D_2$ from the probes 106 and 108 to the planar transmission line 104 is a trade-off between weak coupling (at large D) and strong perturbation of the circuit 102 (at small D). While $D_1$ and $D_2$ do not have to be the same, they can fall in the range between 1 and 10 micron, for example, around 10 micron. The coupling in this range is "near-field," meaning that the electromagnetic mode excited in the dielectric waveguide structure 106B and 108B of the probes propagates through polarization currents $\partial P/\partial T = \chi \partial E/\partial T$, where $\chi$ is the electric susceptibility given by $\chi = \in -1$, where $\in$ is the THz dielectric constant. The polarization current is, in turn, transformed to conduction current by a metallic transforming transmission line (106C and 108C) located well above the dielectric prongs. An example transforming structure (106C and 108C) can be a terminated section of coplanar waveguide (CPW) or other planar transmission-line structure. Tapering of the transmission line may be necessary to achieve acceptable efficiency, and may be achieved by a variety of methods including "adiabatic" transformation as is done in the well-known Klopfenstein coupler at microwave frequencies. As such, because $D_1$ and $D_2$ are not equal to zero, the subject innovation can enable the probes 106, 108 to measure or characterize the device/circuit under test 102 without the probes 106, 108 coming into electrical contact with the planar transmission line 104 in which the device or circuit under test 102 is embedded. This contact-free capability gives the subject innovation the ability to avoid the mechanical stress on the probe 106, 108 and scratch-induced damage (of the sample transmission line 104) that the prior art experiences.

Once the polarization current is transformed to conduction current, the field strength can be measured by an optical fiber-coupled photomixer 108D monolithically embedded into the CPW or other transmission line 106C, 108C at the top of the receiving photomixing probe 108. THz photomixing is well-suited to this task because of its huge operational bandwidth, its spectral purity, and lack of harmonics, spurs, and other non-linear effects that occur when scaling the conventional vector-network analyzer into the THz regime. Photomixing is so pure because the THz tone it generates is exactly the beat frequency $|v_1-v_2|$ between two frequency-offset, single-frequency diode lasers, readily available in either DFB (distributed feedback) or DBR (distributed Bragg reflector) designs. There are no harmonics in this process, nor spurs, because the nonlinearity that the mixing action is based upon is pure quadratic (the fundamental internal photoelectric effect associated with cross-gap absorption in any semiconductor). Assuming it is sinusoidal at frequency f, the incident signal across the transmission line in the receive probe is then down-converted to an intermediate frequency (IF) given by $|f-|v_1-v_2||$.

A notable aspect of the subject innovation is that the THz coupling of the contact-free probe is reciprocal. That is, the coupling to a transmission-line under test 104, and the subsequent transformation to a transmission-line-embedded photomixer, can also operate in reverse. Hence, a THz signal generated by the photomixer 106A will propagate in the probe planar transmission line 106C, transform to a dielectric-waveguide mode in dielectric waveguide structure 106B, and couple to the device or circuit under test 102 through near-field, polarization-current coupling without electrical contact with planar transmission line 104. The signal from the device or circuit under test 102 will couple to the dielectric waveguide structure 108B without electrical contact with planar transmission line 104, transform and propagate to the probe planar transmission line 108C before reaching photomixer 108A.

The operation of the transmit and receive photomixers is based on the same laser-generated THz difference-frequency tone. However, the transmit photomixer 106A must generate a THz signal while the receive photomixer 108A only needs to accept it. This difference can be readily controlled by DC bias. The transmit photomixer 106A can be DC-biased so that the laser-difference-frequency tone transforms DC bias power to AC THz power through photoconductance modulation. The receive photomixer 108A need not be DC biased, in which case an incident THz signal will mix with the laser-difference-frequency tone. Lacking any modulation of the transmit laser signals, this is pure homodyne conversion. To address 1/f and related problems, one of the transmit laser powers can be AM modulated to produce an IF well within the bandwidth of lock-in amplifiers and ultra-low-noise transimpedance amplifiers. This "quasi-homodyne" approach carries the fully advantages of traditional homodyne and heterodyne conversion typically used in vector network analyzers and coherent RF transceivers of all sorts. One significant advantage over incoherent detection (which spectrum analyzers usually do) is signal-to-noise ratio. Homodyne and heterodyne transceivers can routinely operate near the theoretical limits dictated by electronic noise. This provides a very high dynamic range, usually in the range of 50-to-100 dB depending on the frequency band and the electronics involved.

The transmitting photomixer probe 106 and receiving photomixer probe 108 can be driven by the same pair of frequency-offset lasers, so the typical frequency jitter in the diode lasers is cancelled perfectly, meaning that there is an inherent capability to do frequency or phase locking. This assumes, of course, that the jitter is tolerably small compared to the THz frequencies of interest. Modern DBR and DFB lasers both tend to jitter by about 100 MHz or less, or 1 part in $10^4$ of a THz tone, and there is no anticipation of resolution requirements any finer than this in the course of the typical THz device characterization.

Figure 2:
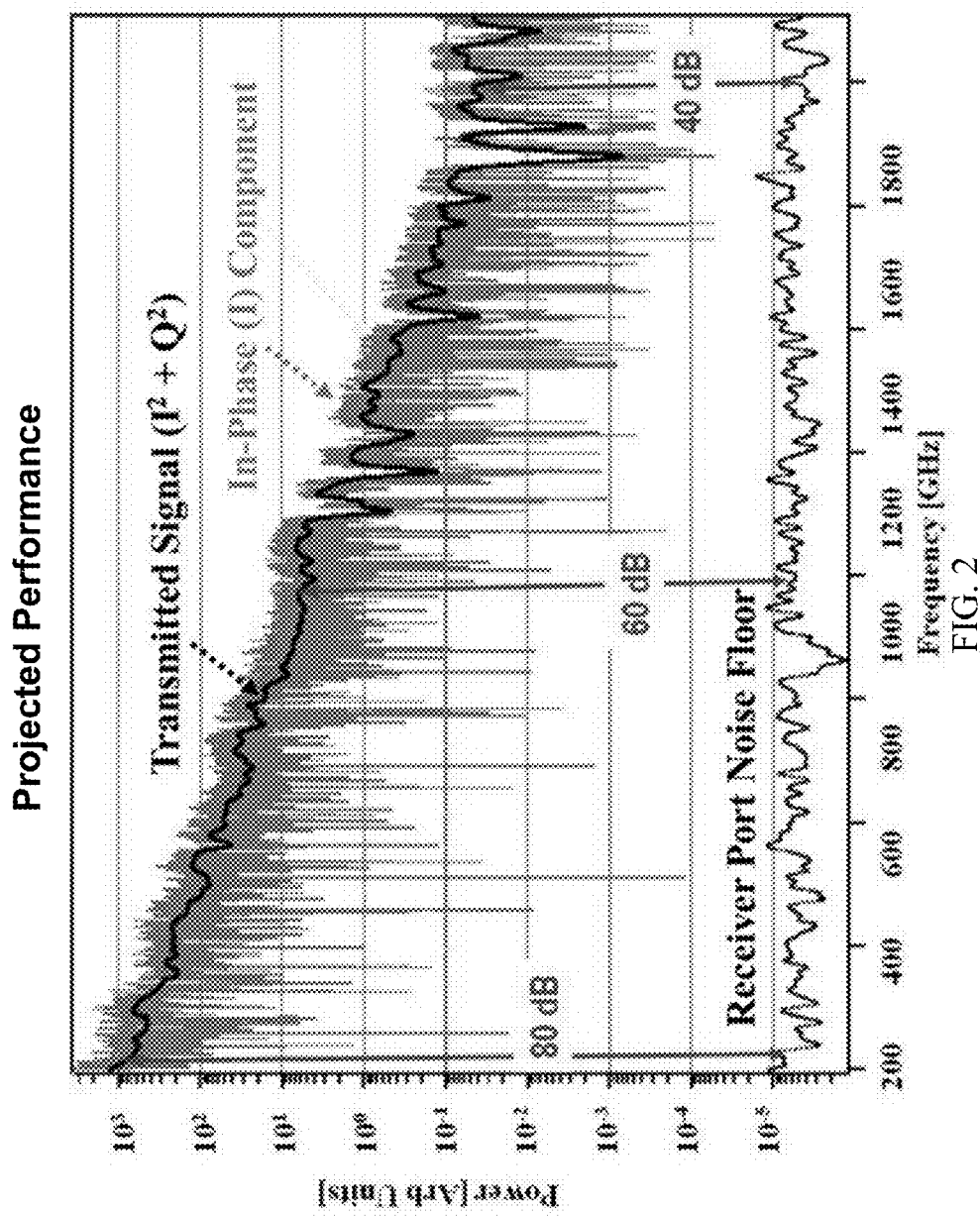
FIG. 2 is an illustrative graph of a typical output signal, noise floor, and signal-to-noise ratio from a coherent photomixing spectrometer.

FIG. 2 illustrates the spectral response, quadrature-component amplitude, and dynamic range of a commercial quasi-homodyne photomixing transceiver (model PB7100 manufactured by Emcore, Corp.). The dynamic range is seen to be 80 dB at 100 GHz, 60 dB at 1.1 THz, and still 40 dB at 2.0 THz. Although the THz radiation propagates as quasi-Gaussian beams rather than the evanescent/surface or dielectric-waveguide modes disclosed herein, the operating principle will be the same, and comparable values of dynamic range are expected once the dielectric probe designs are optimized.

Figure 3:
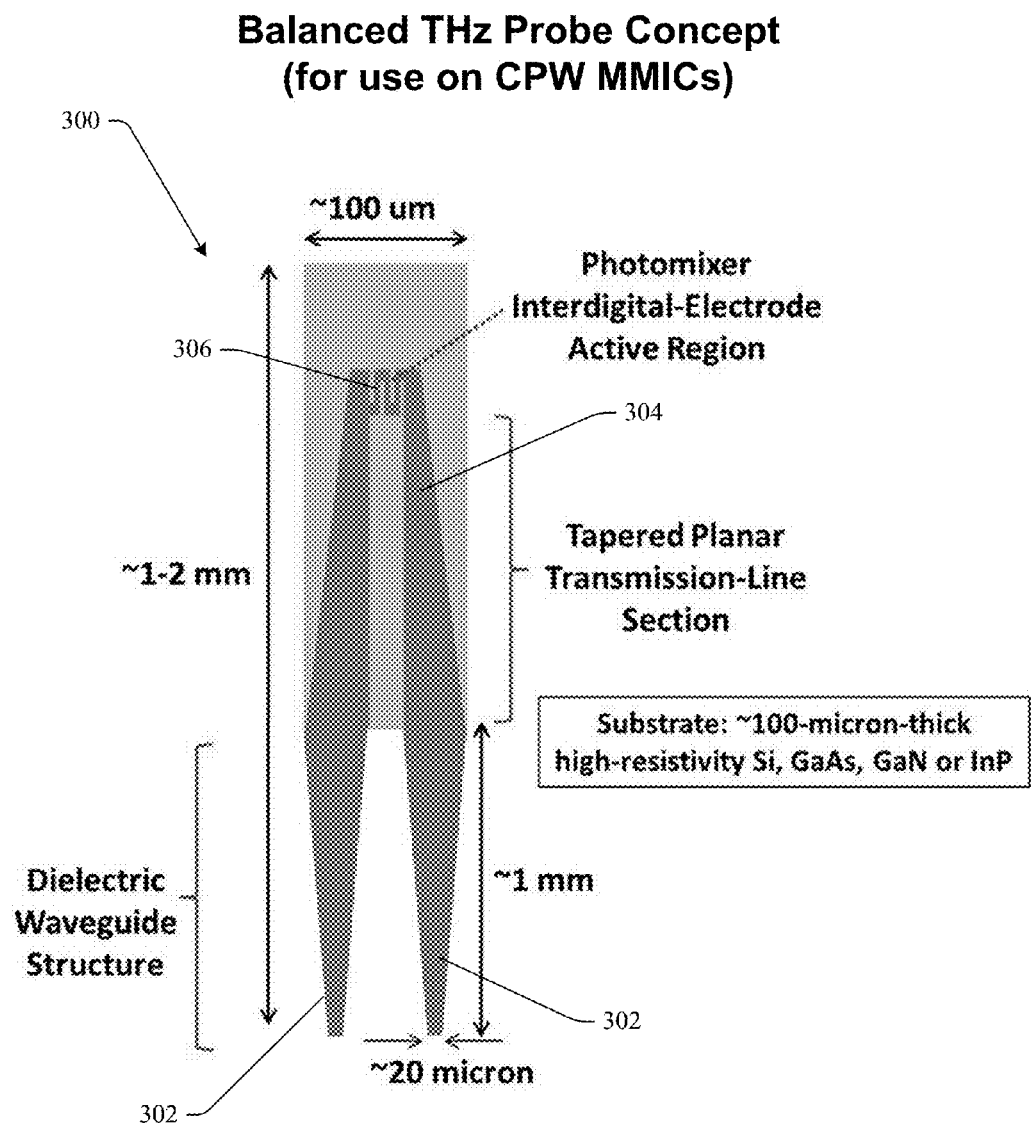
FIG. 3 is a plan view of a proposed balanced "microfork" THz probe structure in accordance with aspects of the innovation.
Figure 4:
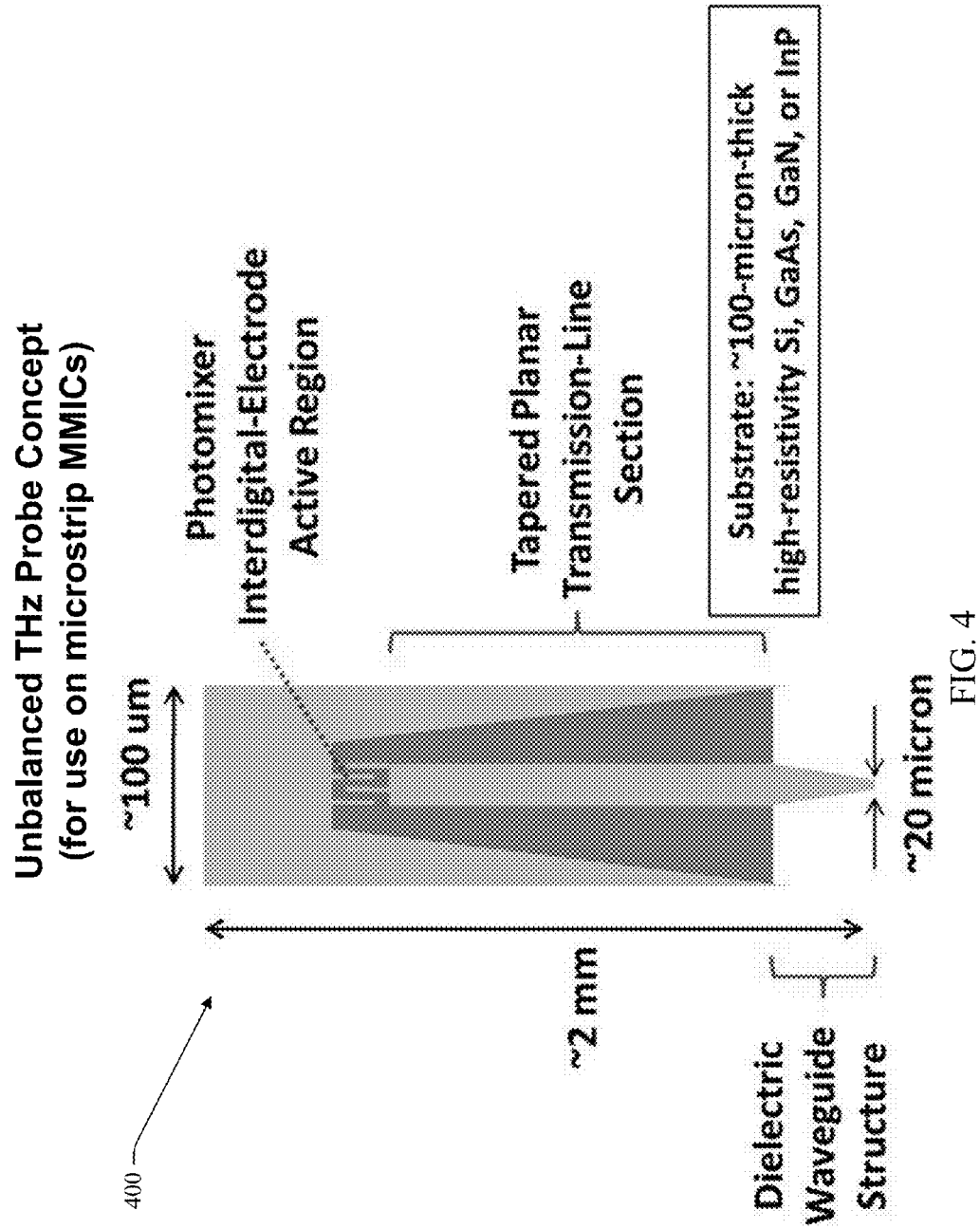
FIG. 4 is a plan view of an unbalanced "microfork" probe structure.

FIG. 3 illustrates a plan view of an example contact-free, ac-coupled probe structure 106 or 108 (hereinafter "probe") in a balanced microfork design configuration that is compatible with a planar transmission line 104 that is a CPW in accordance with aspects of the innovation (FIG. 4 is an illustration of a probe structure 400 in an unbalanced microfork design that is compatible with a planar transmission line 104 that is a microstrip). The probe 300 includes dielectric prongs/dielectric waveguide structure 302, a tapered region/ planar transmission line structure 304 and an interdigital electrode region 306. The probe can be made from a high-resistivity Si, GaAs, InP, or GaN substrate material between, 10 and 1000 microns thick, for example, around 100 microns thick. The overall height of the probe 300 can be between 0.1 and 10 mm, for example, around 1.0 mm high. The dielectric prongs 302 can be between 0.05 and 5 mm high. Further, the bottom portion of each dielectric prong 302 can be between 10 and 100 microns wide.

Figure 5:
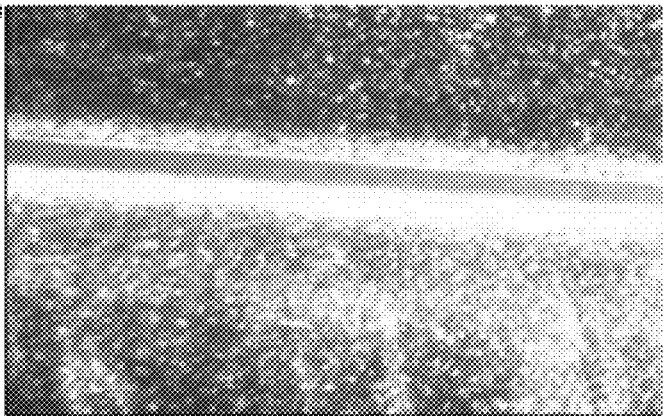
FIG. 5 is an illustration of micrograph views of laser micromachining fabricating techniques in accordance with aspects of the innovation.
Figure 5:
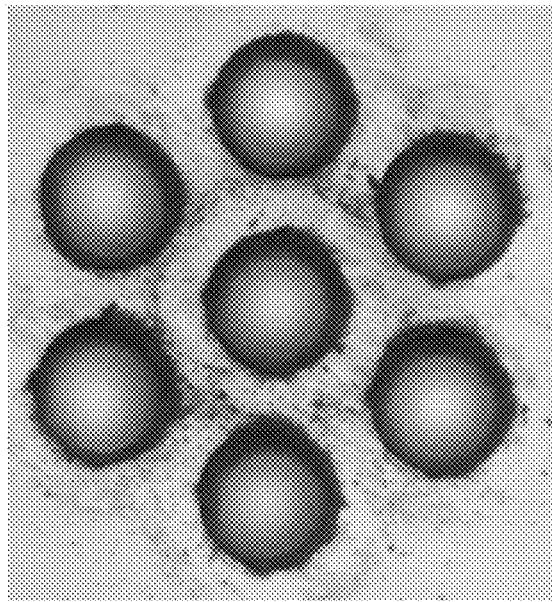
Figure 6:
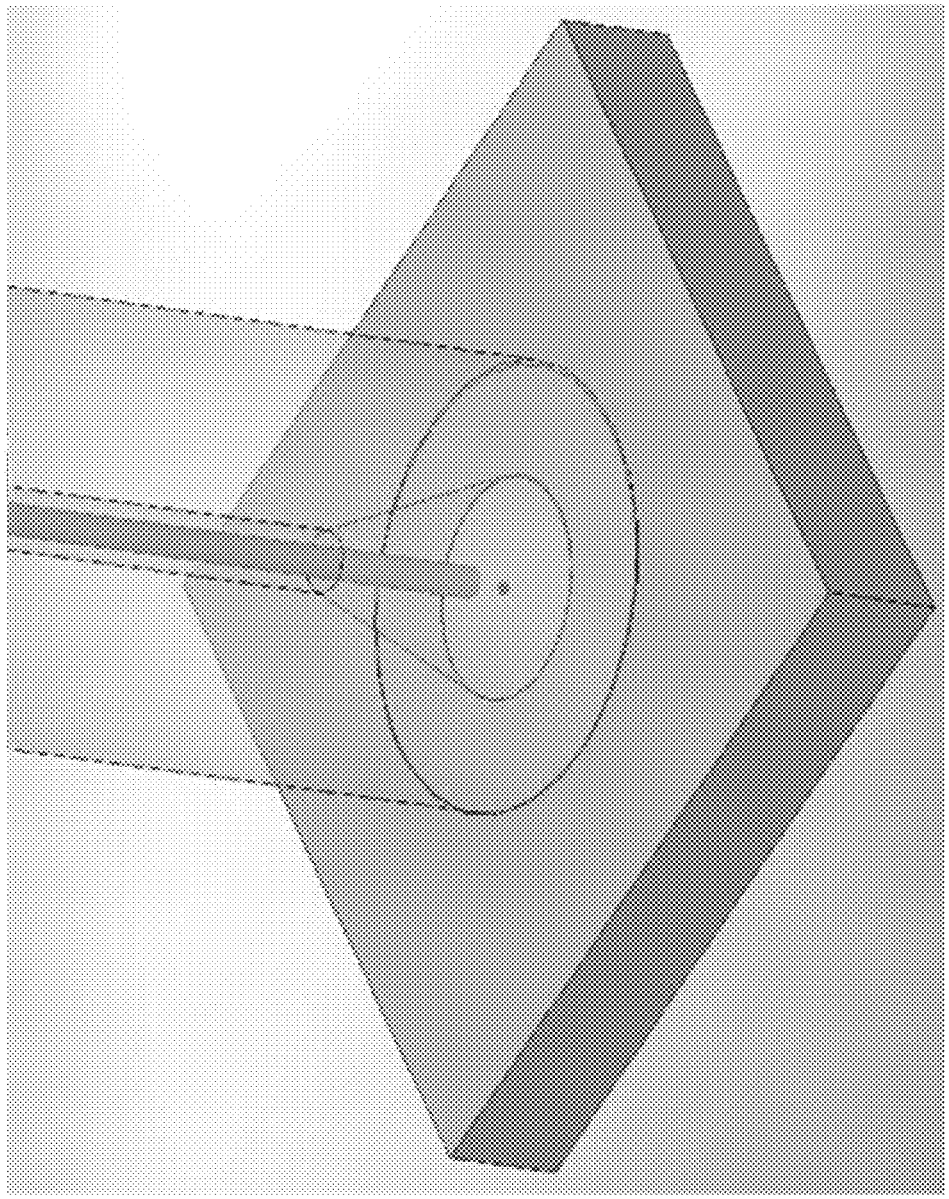
FIGS. 6-9 are illustrations of fabrication techniques in accordance with aspects of the innovation.
Figure 7:
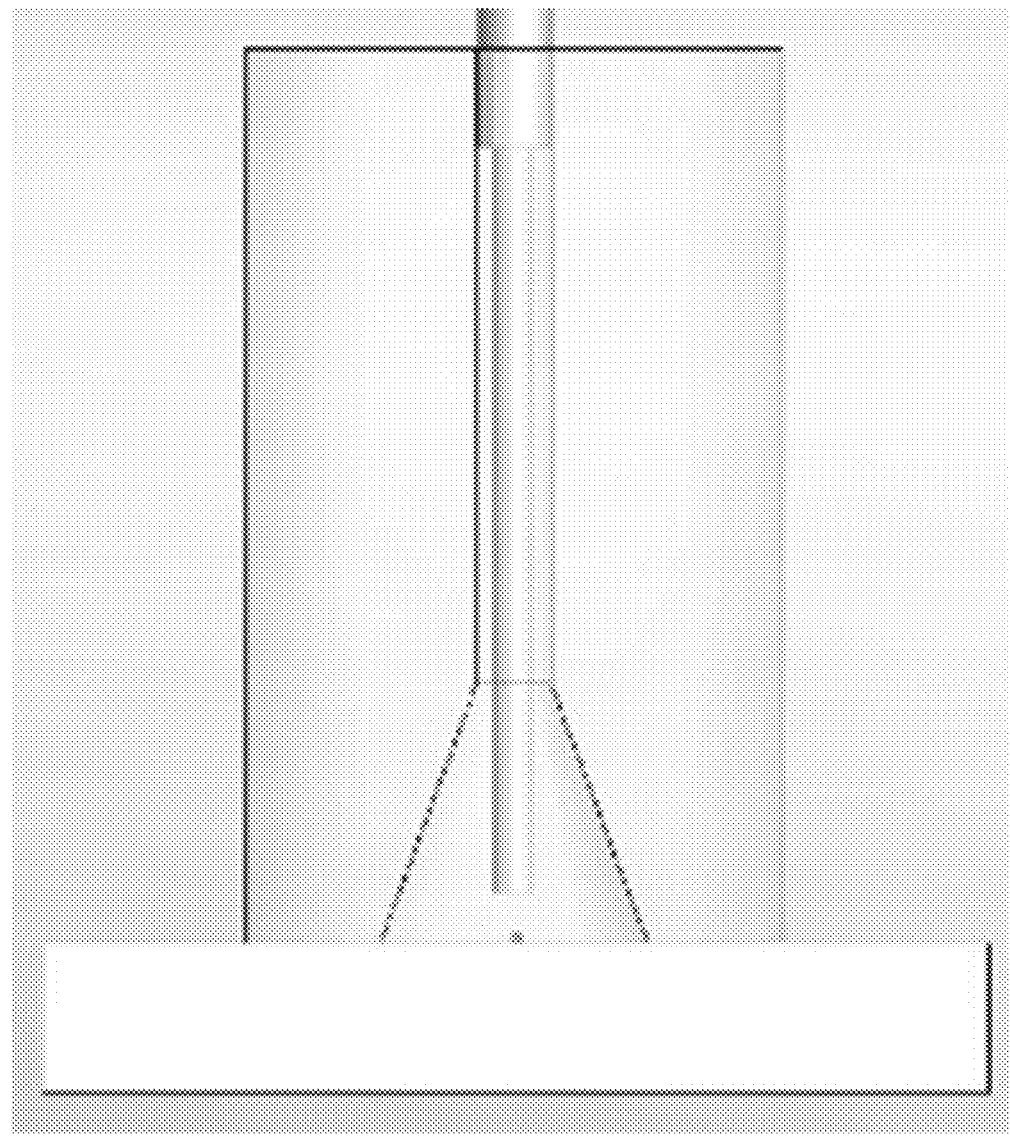
Figure 8:
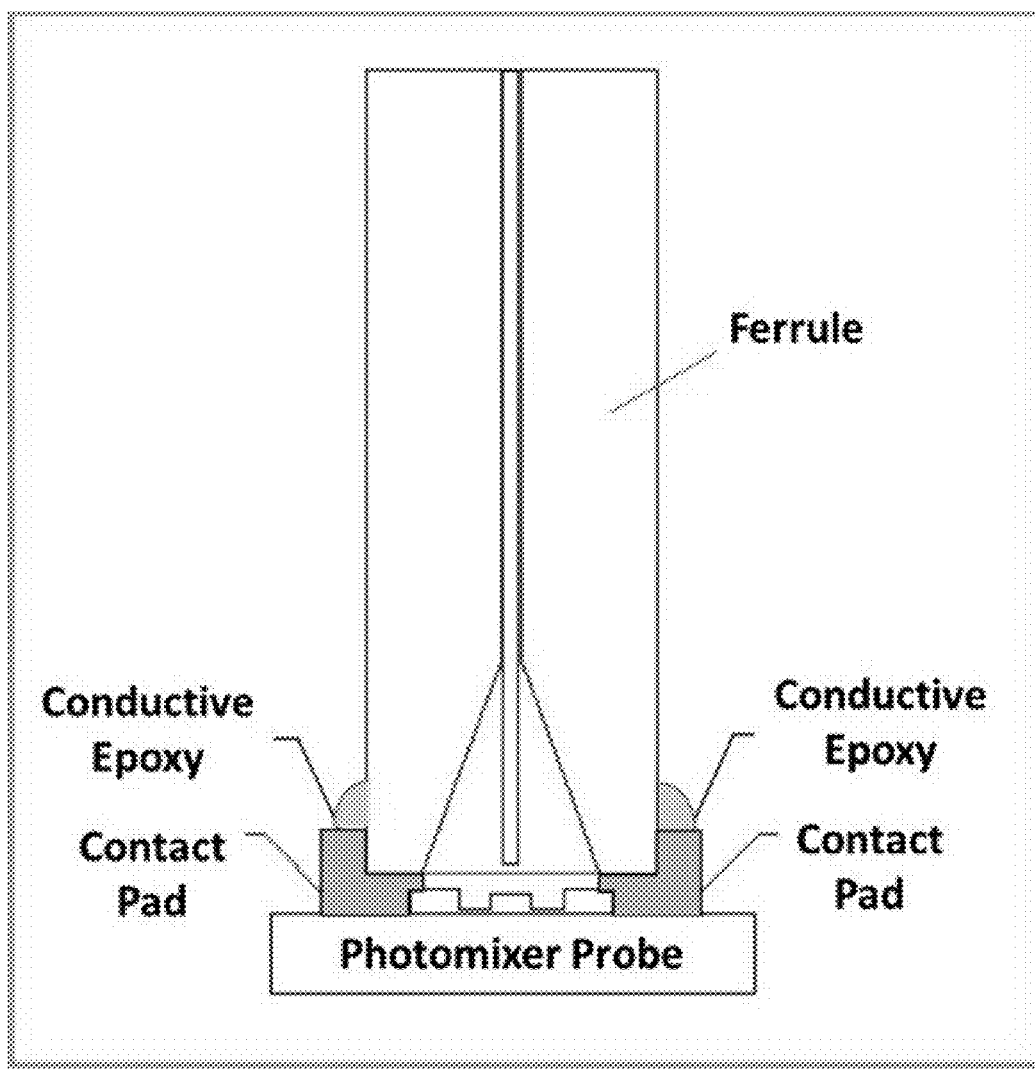
Figure 9:
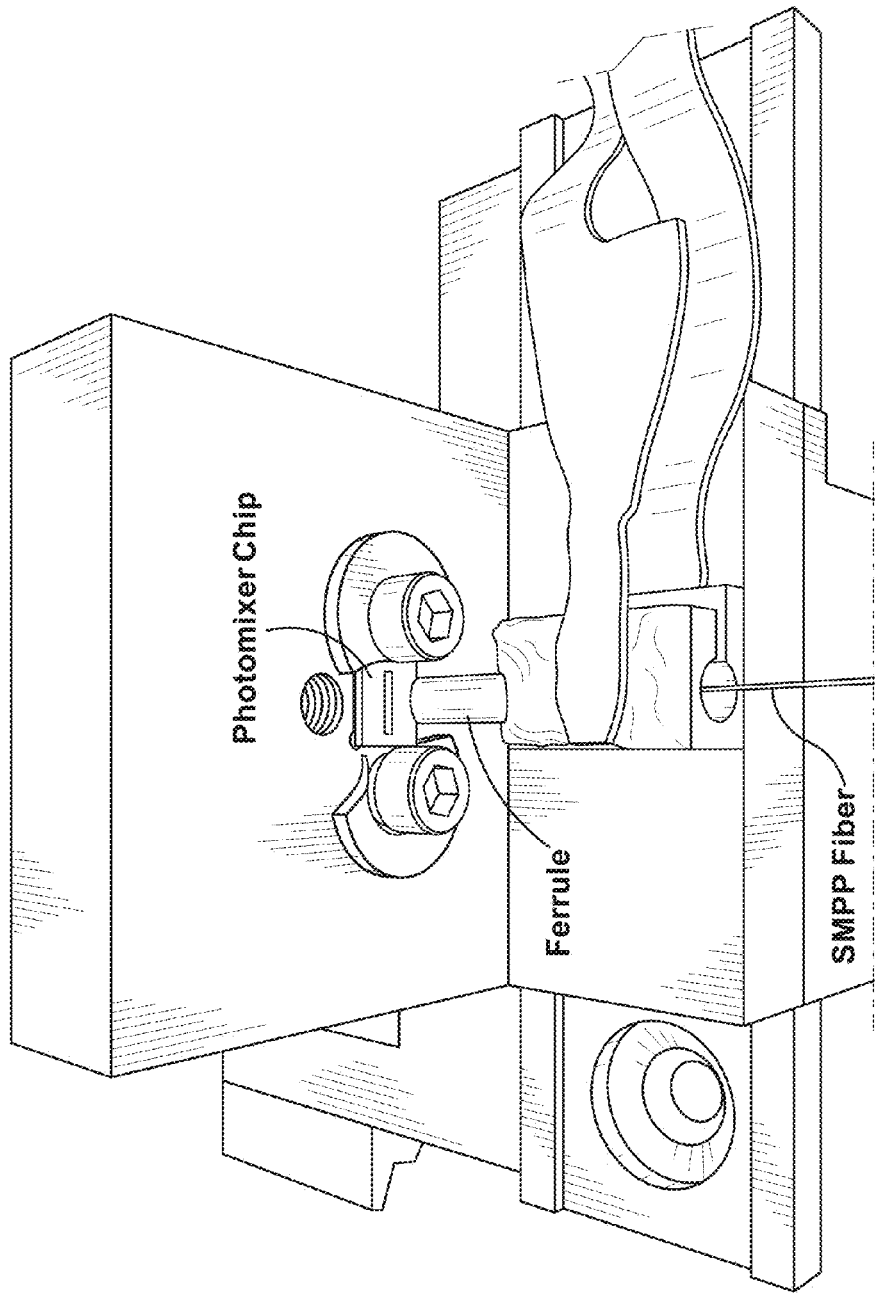

The approximate dimensions illustrated in FIGS. 3 and 4 are based on preliminary design considerations, including the width of the CPW-transmission-line 104 circuit in which the device-under-test 102 is likely to be embedded, the necessary offset of the dielectric-waveguide portion of the probe to the transmission-line circuit, and the area needed for fiber-optic coupling to the photomixer element. It is to be understood, of course, that the specific dimensions provided in connection with example probe 300 are meant to illustrate one possible embodiment, and greater or lesser values can be used in other embodiments, such as where some of these design considerations vary. The non-rectilinear geometry of the "microfork" does not comply with standard dicing or scribe-and-break tools. And because the thickness wants to be approximately 100 micron or more for mechanical strength, wet- or reactive-ion etching of the substrate, be it Si, GaAs, InP, or GaN, would be cumbersome and expensive. Thus, an alternative approach to dicing or scribing of the chips is laser micromachining—a technique that works very well on all common semiconductors and produces small kerf (10s of microns) and nearly vertical smooth sidewalls, see FIG. 5. This can be accomplished via high peak-power Q-switched solid-state (e.g., Nd:YAG) lasers that have become very popular in microelectronic fabrication the past decade. The dicing action occurs by laser ablation, which can penetrate up to several hundred microns over a short period of time (minutes). And complex chip shapes and sizes can be obtained by routing the laser beam with mirrors mounted on precision translation stages.

The Si-, GaAs-, InP-, or GaN-based photomixers and associated circuitry can be fabricated by standard methods developed over the past decade. This includes interdigital electrodes defined in the photoconductive gap of the probe transmission line. The ultrafast Si-, GaAs-, InP-, or GaN-based active layers will either be implanted Si, epitaxial low-temperature-grown (LTG) GaAs, epitaxial ErAs:GaAs, or some form of InGaAs epitaxial film (lattice-matched to InP) developed by materials scientists over the past few decades.

A second fabrication challenge exists in fiber-coupling of the diode lasers to the Tx and Rx photomixing probes 106, 108. The GaAs-based photomixers work best with 780-nm laser diodes, which are available as commercial off-the-shelf (COTS) components. But 780-nm fiber is not as easy to couple into and out-of single-mode fiber as the standard 9-micron-core fiber so common in 1550-nm optical telecommunications. The ~6 micron core of 780-nm fiber is much more lossy and fragile than 1550-nm fiber, so must be butt-coupled with special machines common to the fiber-optic industry.

Referring to FIGS. 6-9, other manufacturers have been identified as having a vast experience in fiber-coupling at both 1550 and 780 nm; techniques of these manufacturers can be employed in fabricating probes of the subject innovation. Their bonding technique involves precision fiber alignment using laser-radiation-induced photocurrent as the alignment metric. After the fiber is in place, a photo-active epoxy is applied and then cured with UV light. They routinely perform fiber packaging for a variety of fiber-coupled instruments that necessarily have to be field-deployable, so can survive manipulation, vibration, elevated temperature, and moisture.

One challenge created by the THz probe technology is the electromagnetics. Dielectric rod antennas have never been scaled to be used at THz frequencies. And although they are fairly common at microwave frequencies, it is not clear whether the design rules that have been developed apply to THz frequencies because these antennas are generally used for standard far-field transmit and receive functions, not the near-field coupling as required by our probe technology. Hence, research on the coupling included full-wave electromagnetic simulation. Electromagnetic simulation at THz frequencies using High Frequency Structure Simulator (HFSS) is still probably the best option in the numerical simulation industry. Research conducted in connection with the subject innovation used HFSS-12 to model and design the photomixer probes over a huge range of frequencies from roughly 100 GHz to 2.0 THz, and as expected, the coupling to the probe increases with frequency.

Once an optimal design is obtained in simulation, there is the required step of verifying the performance experimentally. This is especially important at THz frequencies where various practical effects, such as surface roughness, can introduce extraneous losses that are nearly impossible to simulate realistically. A related challenge of any high-frequency probe technology, dc- or ac-coupled, is calibration. What nearly every engineer desires from high-frequency probing of any device are the associated scattering (S) parameters. For two-port devices these can be obtained accurately only through a careful calibration procedure, the standard one utilizing "SOTL" standards (short, open, through, load). And such calibration is critical to the success of standard vector network analysis at all frequencies. Unfortunately, such SOTL standards do not exist for the subject innovation, and it is not even clear how to fabricate them. Therefore, an important aspect of the innovation is the ability to carry out cross-calibration. The photomixer probe technology can easily work down to 100 GHz or lower, thereby overlapping the frequency range of existing VNAs, which operate up to ~500 GHz. Thus, the subject innovation can utilize a common, shared test structure compatible with both conventional techniques and the innovative probing techniques of the subject innovation. This can allow the use of standard-VNA S parameters to quantify the photomixer probe performance.

Given the anticipated levels of signal-to-noise ratio of the photomixer "microfork" probes (at least 50 dB) and comparable levels of dynamic range, another possibility is characterization of prospective THz devices by measurement of the noise spectrum. It is often true that the noise spectrum from solid-state devices is governed by the same device physics and forward transfer function as the signal spectrum. In the case of transistors, the output noise will be present even if the forward gain is very low, as required by thermodynamics. And at the high bias and current density levels that THz solid-state devices tend to require, the shot-noise and thermal-noise effects are bound to be very strong. Of course, this may require long integration times and tedious data acquisition, but the noise spectrum could provide important diagnostic information about devices in which amplification is not even possible.

Figure 10:
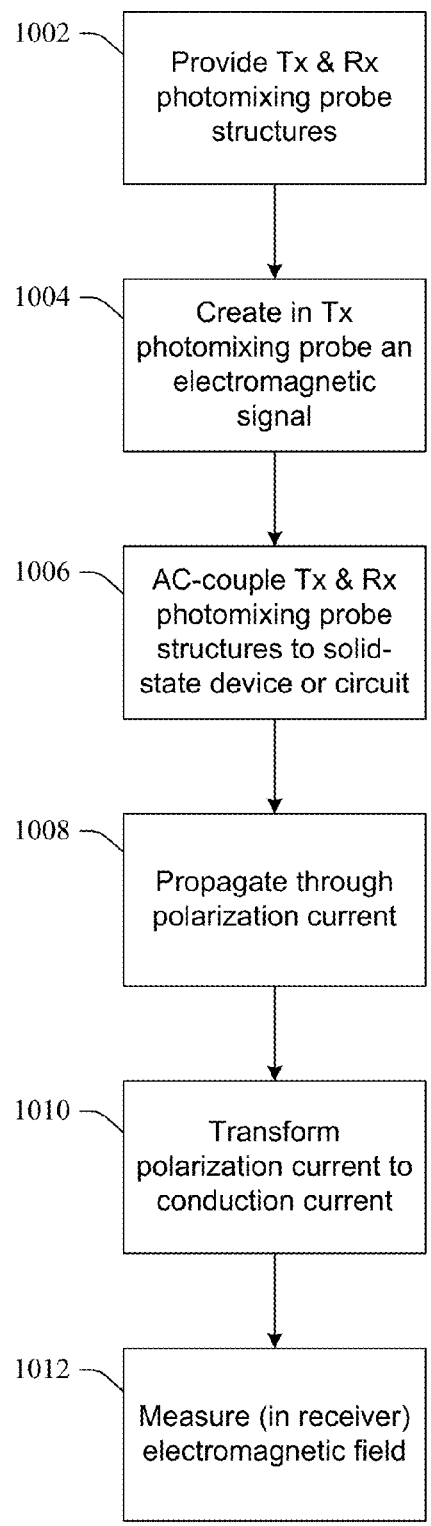
FIG. 10 displays the physical methodology behind the proposed technique of measuring or characterizing a solid-state device or integrated circuit with contact-free probes at frequencies up to 1.0 THz and beyond in accordance with aspects of the innovation.

FIG. 10 is an illustration of the physical methodology of measuring or characterizing a solid-state device or circuit under test having a frequency up to 1.0 THz and beyond in accordance with aspects of the innovation. At 1002, a Tx photomixing probe structure 106 and a Rx photomixing probe structure 108 can be provided. At 1004, the Tx photomixing probe structure 106 creates an electromagnetic signal. At 1006, the Tx photomixing probe structure 106 and the Rx photomixing probe structure 108 can be ac-coupled to the solid-state device or circuit under test 102 via an electromagnetic field, i.e. without electrical contact between the probes 106, 108 and the planar transmission line 104. At 1008, the ac-coupling can occur by an electromagnetic mode excited in the Tx photomixing probe structure and the Rx photomixing probe structure, and can propagate through polarization currents. In each probe 1010, the polarization current can be transformed to conduction current, or vice versa. At 1012, once the polarization current is transformed to conduction current, the electromagnetic field strength created by the Tx photomixing probe structure 106 can be measured by the Rx photomixing probe structure 108.

Figure 11A:
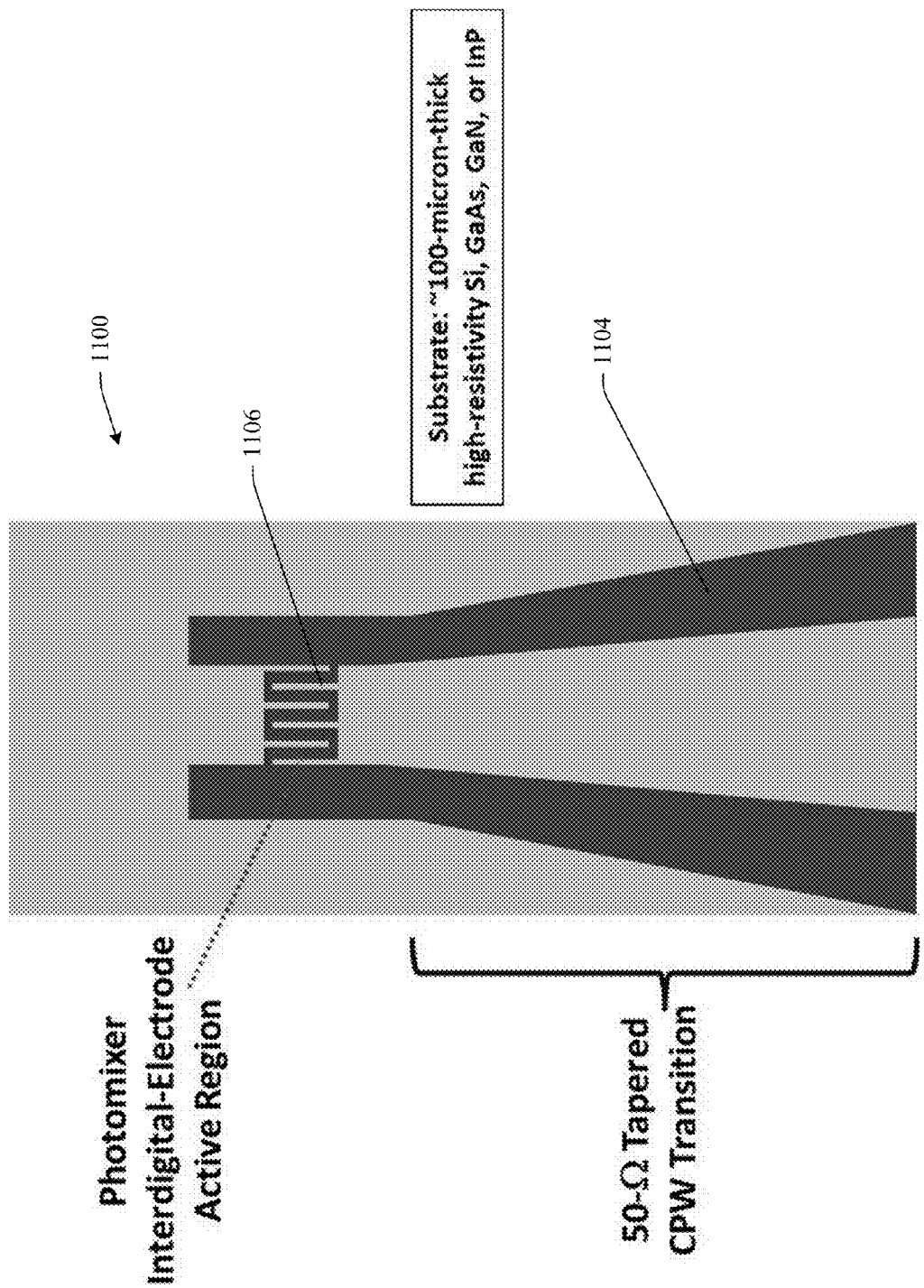
Figure 12A:
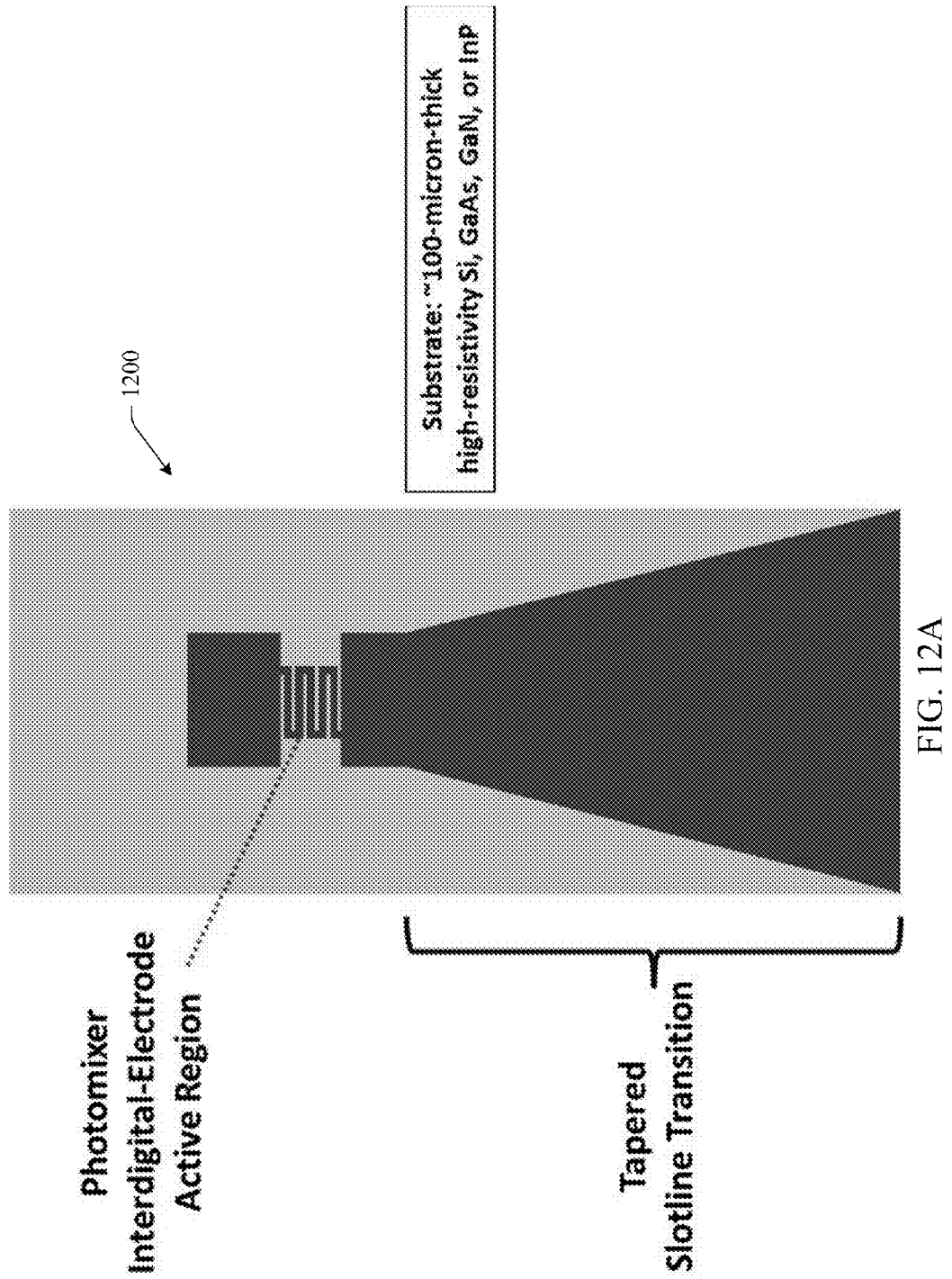
FIGS. 12A-B show a plan view of a proposed "orthorhombic" THz probe structure in accordance with aspects of the innovation, and designed with slot-line coupling for measuring signals in similar unbalanced circuits such as that shown in FIG. 12B.

FIG. 11A illustrates a plan view of an alternative contact-free, ac-coupled probe structure 106, 108 in a balanced "orthorhombic" design configuration compatible with the CPW planar transmission line 104 in accordance with aspects of the innovation (FIG. 12A is an illustration of a corresponding probe structure 1200 that is an unbalanced orthorhombic design configuration, compatible with microstrip, etc). The "orthorhombic" probes 1100 and 1200 differ from the "microfork" structure of FIGS. 3 and 4 in that dielectric-waveguide structure of the microfork is eliminated. Instead, the tapered transmission-line section common to all probes of the subject innovation can start at the bottom of the probe—the end closest to the transmission-line 104 under test. In other words, the "orthorhombic" design includes the tapered, coplanar-waveguide region 1104 and an interdigital-electrode photomixer 1106, but does not have the prongs of the "microfork" design shown in FIG. 3 or 4. The probe can be made from a high-resistivity Si, GaAs, InP, or GaN substrate material between 50 and 500 microns thick. The overall width of the probe 1100 can be between 10 and 100 micron, consistent with the size of planar transmission lines used in integrated circuits at frequencies up to 1 THz and beyond.

Figure 12B:
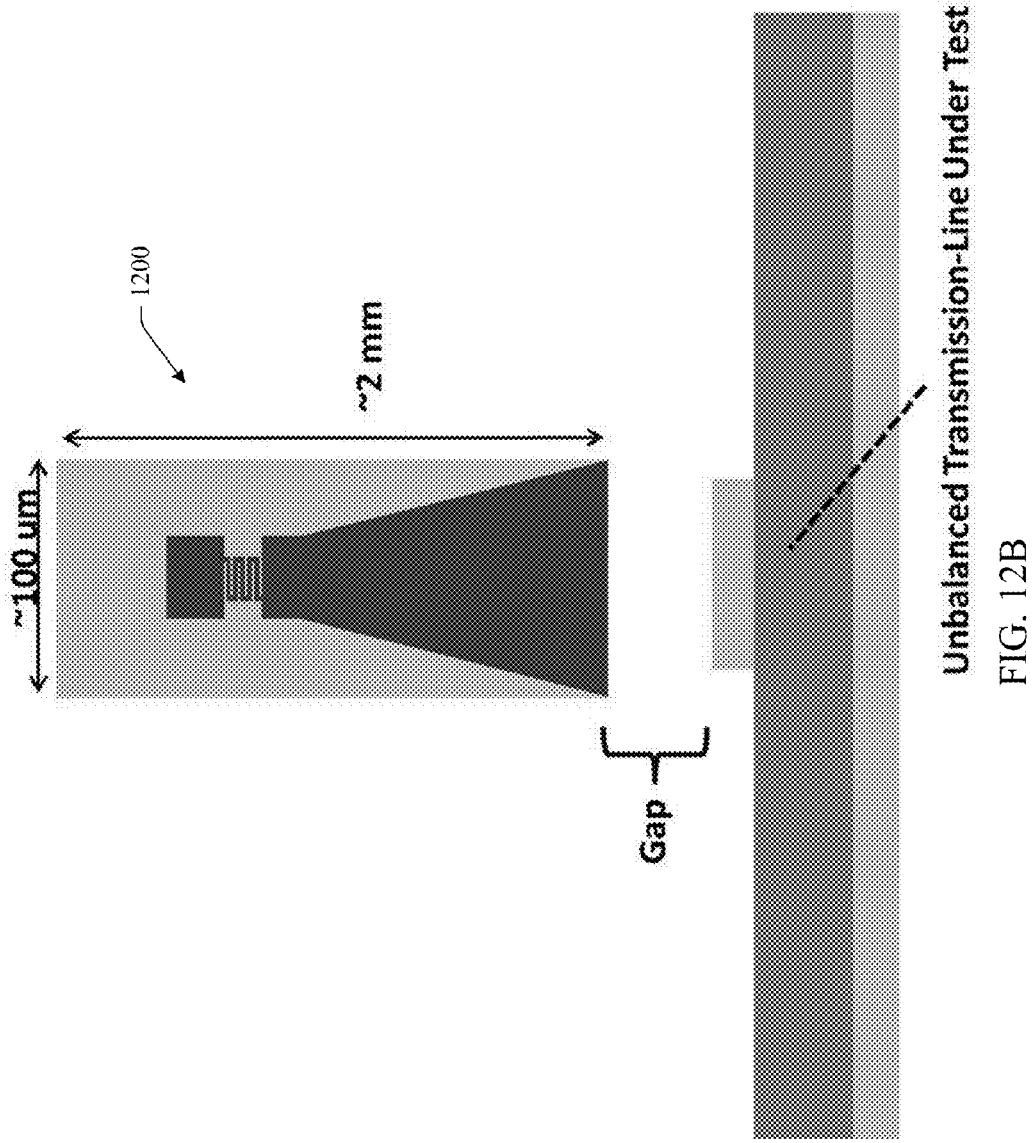

The approximate dimensions illustrated in FIGS. 11B and 12B are based on preliminary design considerations, including the width of the balanced or unbalanced transmission-line circuit in which the device-under-test is likely to be embedded and the area needed for fiber-optic coupling to the photomixer element. The size of the gap distance shown in FIGS. 11B and 12B is again a tradeoff between strong coupling to the transmission line under test and strong perturbation of the transmission line signal, both of which depend inversely on gap size. The rectilinear geometry of the "orthorhombic" probe complies with standard dicing and scribing tools, so it does not necessarily require the intricate laser micromachining of the "microfork" described earlier. However, such laser micromachining may be necessary for accuracy and surface-morphology (i.e., smoothness) reasons.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. In addition, while the subject innovation uses examples with THz signals, it is applicable to signals with other frequencies, especially within the range of 0.5 THz to 1.6 THz.

What is claimed is:

1. A device for measuring or characterizing a solid-state device or an integrated circuit at frequencies up to 1.0 THz and beyond comprising:
    a transmitting photomixing probe; and
    a receiving photomixing probe;
    wherein each of the transmitting photomixing probe and the receiving photomixing probe comprise a photomixer and optical fibers, and
    wherein the transmitting photomixing probe and the receiving photomixing probe are ac-coupled to the solid-state device or the integrated circuit via an electromagnetic field, and are not in physical contact with the solid-state device or the integrated circuit.

2. The device of claim 1, wherein each of the transmitting photomixing probe and the receiving photomixing probe comprise two optical fibers directly coupling the photomixer to two lasers that are external to the photomixing probe.

3. The device of claim 2, wherein the lasers have a mutually coherent but tunable frequency difference.

4. The device of claim 2, wherein the lasers are both single frequency diode lasers.

5. The device of claim 1, wherein the transmitting photomixing probe and the receiving photomixing probe each comprise a high resistivity substrate and a metalized surface.

6. The device of claim 5, wherein the substrate is selected from the group consisting of silicon (Si), gallium arsenide (GaAs), indium phosphide (InP), gallium nitride (GaN), or a combination of two or more thereof.

7. The device of claim 1 wherein the solid-state device or the integrated circuit is embedded in a planar transmission line, and wherein an output from the solid-state device or integrated circuit is sampled in the planar transmission line.

8. The device of claim 7, wherein the distance ($D_1$) between the transmitting photomixing probe and the planar transmission line and the distance ($D_2$) between the receiving photomixing probe is in the range of about 1 micron to about 100 microns.

9. The device of claim 8, wherein $D_1$ and $D_2$ are each in the range of about 1 micron to about 10 microns.

10. The device of claim 7, wherein neither the transmitting photomixing probe nor the receiving photomixing probe come into electrical contact with the planar transmission line.

11. The device of claim 7, wherein the planar transmission line is selected from the group consisting of a coplanar waveguide, a slot-line, a microstrip, or a twin line.

12. The device of claim 1, wherein the transmitting photomixing probe and the receiving photomixing probe have a fork-like configuration or an orthorhombic configuration.

13. The device of claim 1, wherein the each of the transmitting photomixing probe and the receiving photomixing probe further comprise a circuit end that is closer to the solid-state state device or the integrated circuit and a dielectric waveguide structure at the circuit end.

14. A method of measuring a solid-state device or an integrated circuit at an RF frequency of up to 1.0 THz and beyond comprising:
   providing a transmitting photomixing probe and a receiving photomixing probe; wherein each of the transmitting photomixing probe and the receiving photomixing probe comprise a photomixer and optical fibers,
   embedding the solid-state device or the integrated circuit in a planar transmission line; and
   ac-coupling the transmitting photomixing probe and the receiving photomixing probe to the solid-state device or the integrated circuit via an electromagnetic field, such that neither the transmitting photomixing probe nor the receiving photomixing probe are in physical contact with the solid-state device or the integrated circuit.

15. The method of claim 14, further comprising sampling an output from the solid-state device or integrated circuit in the planar transmission line.

16. The method of claim 14, wherein the ac-coupling occurs by interacting a polarization current in at least one of the transmitting photomixing probe or the receiving photomixing probe and a fringing field just above the solid-state device of the integrated circuit.

17. The method of claim 16, further comprising transforming the polarization current to a conduction current in the at least one of the transmitting photomixing probe or the receiving photomixing probe, and wherein once the polarization current is transformed to the conduction current, generating an electromagnetic field, and measuring the strength of the electromagnetic field with the receiving photomixing probe.

18. The method of claim 16, further comprising transforming a conduction current to a polarization current in at least one of the transmitting photomixing probe or the receiving photomixing probe; generating an electromagnetic field; and measuring the strength of the electromagnetic field.

19. The method of claim 14 further comprising modulating at least one of the transmitting photomixing probe or the receiving photomixing probe via amplitude modulation or frequency modulation.

20. The method of claim 19, wherein the signal from the transmitting photomixing probe is modulated via amplitude modulation or frequency modulation.

* * * * *

UNITED STATES PATENT AND TRADEMARK OFFICE
CERTIFICATE OF CORRECTION

PATENT NO. : 9,823,187 B2  
APPLICATION NO. : 15/345344  
DATED : November 21, 2017  
INVENTOR(S) : Elliott R. Brown Page 1 of 1

It is certified that error appears in the above-identified patent and that said Letters Patent is hereby corrected as shown below:

In the Specification

Column 1, starting at Line 20, the Notice on Government Funding:
This innovation was made with government support under a grant awarded by the Office of Naval Research (ONR) Award N00014-11-1-0721. The government has certain rights in the innovation.

Should read:
This invention was made with government support under N00014-11-1-0721 awarded by Office of Naval Research. The government has certain rights in the invention.

Signed and Sealed this
Eighteenth Day of December, 2018

Andrei Iancu
*Director of the United States Patent and Trademark Office*